United States Patent [19]
Denis et al.

[11] Patent Number: 5,420,346
[45] Date of Patent: May 30, 1995

[54] PREPARATION OF ADIPIC ACID BY HYDROCARBOXYLATION OF PENTENIC ACIDS

[75] Inventors: Philippe Denis, Decines; Jean-Michel Grosselin, Francheville; Francois Metz, Vernaison, all of France

[73] Assignee: Rhone-Poulenc Chimie, Courbevoie, France

[21] Appl. No.: 953,092

[22] Filed: Sep. 29, 1992

[30] Foreign Application Priority Data

Oct. 3, 1991 [FR] France .................................. 91 12392

[51] Int. Cl.⁶ ............................................. C07C 51/14
[52] U.S. Cl. ................................................... 562/522
[58] Field of Search ......................................... 562/522

[56] References Cited

U.S. PATENT DOCUMENTS 3,579,551 5/1971 Craddock et al. .
3,816,490 6/1974 Forster .................................. 562/522
4,788,333 11/1988 Burke .................................... 562/517

OTHER PUBLICATIONS

Catalysis Reviews, vol. 23, No. 1&2, (1981) pp. 89–105.

*Primary Examiner*—Paul J. Killos
*Assistant Examiner*—Joseph Conrad
*Attorney, Agent, or Firm*—Burns, Doane, Swecker & Mathis

[57] ABSTRACT

Adipic acid is selectivity prepared by reacting water and carbon monoxide with at least one pentenic acid, in the presence of a catalytically effective amount of an iridium-based catalyst and at least one iodinated promoter therefor at an elevated temperature, at a pressure greater than atmospheric and in at least one solvent medium which comprises a saturated aliphatic or cycloaliphatic hydrocarbon or halogenated derivative thereof, an aromatic hydrocarbon or halogenated derivative thereof, or an aliphatic, aromatic or mixed ether, and wherein the I/Ir atomic ratio is less than 20.

14 Claims, No Drawings

PREPARATION OF ADIPIC ACID BY HYDROCARBOXYLATION OF PENTENIC ACIDS

BACKGROUND OF THE INVENTION

1. Field of the Invention

The present invention relates to the preparation of adipic acid by hydrocarboxylation of pentenic acids, and, more especially, to the preparation of adipic acid by reacting water and carbon monoxide with at least one pentenic acid.

2. Description of the Prior Art

U.S. Pat. No. 3,579,551 describes the preparation of carboxylic acids by reacting ethylenically unsaturated compounds with carbon monoxide and water in the presence of a catalytic composition, essentially comprising compounds or complexes of iridium, and an iodinated promoter. The ethylenically unsaturated compounds are selectively converted into carboxylic acids (linear and branched) by conducting the reaction, preferably in liquid phase, at a temperature ranging from 50° to 300° C. (preferably from 125° to 225° C.), under carbon monoxide partial pressures advantageously ranging from 5 to 3000 psia or, more specifically, from 25 to 1000 psia.

Any source of iridium appears to be suitable and various sources of iodinated promoters are indicated; the I/Ir atomic ratio can vary over wide limits (1:1 to 2,500:1) and preferably from 3:1 to 300:1.

The liquid reaction medium can contain any solvent which is compatible with the catalytic system, $C_2$–$C_{20}$ monocarboxylic acids being the preferred solvents.

Example 1 of this '551 patent, carried out using a propylene starting material, indicates that such a system favors the formation of branched carboxylic acids (isobutyric).

Example 19 thereof, carried out using 1-hexene, confirms the extent of the proportion of branched carboxylic acids thus obtained.

This disadvantage (lack of selectivity in respect of linear carboxylic acids) is conspicuously apparent. Indeed, in U.S. Pat. No. 3,816,489 it is proposed to conduct the subject reaction employing an I/Ir atomic ratio ranging from 3:1 to 100:1 in order predominantly to obtain terminal carboxylic acids.

Although such techniques are of considerable interest to this art, notably in the case of starting materials comprising olefinically unsaturated compounds otherwise devoid of reactive functional groups and, in particular, in the case of the olefins themselves, many difficulties are encountered in extrapolating these techniques to starting materials which contain, in addition to the site of ethylenic unsaturation, a functional group which is reactive under the conditions of the subject reaction.

Indeed, the initial attempts conducted in the laboratories of the assignee hereof to extrapolate such techniques using pentenic acid starting materials were unsuccessful, because reactions other than those intended were effected by reason of the —COOH functional group borne by the ethylenically unsaturated starting compound.

SUMMARY OF THE INVENTION

Accordingly, a major object of the present invention is the provision of an improved process for the hydrocarboxylation of pentenic acids exhibiting an appreciable selectivity for adipic acid.

Briefly, the present invention features a process for preparing adipic acid by reacting water and carbon monoxide with at least one pentenic acid, in the presence of an iridium-based catalyst and at least one iodinated promoter therefor, at a high temperature, at a pressure greater than atmospheric pressure, in at least one solvent selected from among the saturated aliphatic or cycloaliphatic hydrocarbons and the halogenated derivatives thereof, the aromatic hydrocarbons and halogenated derivatives thereof and the aliphatic, aromatic or mixed ethers, and wherein the I/Ir atomic ratio is less than 20.

DETAILED DESCRIPTION OF THE PREFERRED EMBODIMENTS OF THE INVENTION

More particularly according to the present invention, by "pentenic acid" is intended penten-2-oic acid, penten-3-oic acid or penten-4-oic acid and mixtures thereof.

Penten-4-oic acid provides good results, but is not readily available.

Penten-3-oic acid, either alone or in admixture with its isomers, is more particularly suitable, given its availability and the satisfactory results which it provides.

The process according to the present invention requires the presence of an iridium-based catalyst. Various sources of iridium can thus be used.

Exemplary sources of iridium suitable for use in the process of the invention include the following:

Metallic Ir: $IrO_2$; $Ir_2O_3$;
IcRl$_3$; $IrCl_3 \cdot 3H_2O$;
$IrBr_3$; $IrBr_3 \cdot 3H_2O$
$IrI_3$;
$Ir_2(CO)_4Cl_2$; $Ir_2(CO)_4I_2$;
$Ir_2(CO)_8$; $Ir_4(CO)_{12}$;
$Ir_2(CO)[P(C_6H_5)_3]_2I$;
$Ir_2(CO)[P(C_6H_5)_3]_2Cl$;
$Ir[P(C_6H_5)_3]_3I$;
$HIr[P(C_6H_5)_3]_3(CO)$;
$Ir(acac)(CO)_2$;
$[IrCl(Cod)]_2$;
(Cod: 1,5-cyclooctadiene; acac: acetylacetonate).

More particularly preferred according to the present invention are $[IrCl(Cod)]_2$; $Ir_4(CO)_{12}$ and $Ir(acac)(CO)_2$.

The amount of iridium to be used can vary over wide limits.

In general, an amount, expressed in mole of metallic iridium per liter of reaction mixture, ranging from $10^{-3}$ to $10^{-1}$ provides satisfactory results. Lesser amounts can be used; however, the reaction velocity is observed to be low. Greater amounts present disadvantages only from an economic standpoint.

Preferably, the concentration of iridium ranges from $5 \times 10^{-3}$ to $10^{-1}$ mol/l, inclusive.

By "iodinated promoter" is intended HI and the organoiodine compounds that generate HI under the conditions of the reaction and, in particular, the $C_1$–$C_{10}$ alkyl iodides. Preferably, HI is employed.

In an essential embodiment of the present invention, the amount of iodinated promoter used is such that the I/Ir molar ratio is less than 20. It proves to be desirable that this ratio be higher than or equal to 0.1. preferably, the I/Ir molar ratio is less than 10. More preferably, such ratio ranges from 1 to 5, inclusive.

The presence of water is also required to conduct the process according to the present invention. In general, the amount of water to be used is such that the water/- pentenic acid(s) molar ratio ranges from 1 to 10, inclusive.

The lesser amount presents the disadvantage of limiting the degree of conversion. A greater amount is not desirable due to the attendant loss in catalytic activity.

In another essential characteristic of the present invention, the reaction is carried out in at least one solvent selected from among the saturated aliphatic or cycloaliphatic hydrocarbons and halogenated derivatives thereof, the aromatic hydrocarbons and halogenated derivatives thereof and the aliphatic, aromatic or mixed ethers.

The precise nature of the solvent selected from among those indicated above is not critical, provided that the latter is in the liquid state under the particular reaction conditions.

Exemplary such solvents include benzene, toluene, chlorobenzene, methylene chloride, 1,2-dichloroethane, hexane, cyclohexane and diphenyl ether.

The amount of solvent present in the reaction mixture can vary over wide limits, for example from 10% to 99%, inclusive, by volume of the reaction mixture. Preferably, this amount ranges from 30% to 90% by volume, inclusive.

As indicated above, the subject reaction is advantageously carried out under a pressure greater than atmospheric pressure and in the presence of carbon monoxide.

It is possible to use carbon monoxide which is substantially pure or of technical quality, such as is commercially available.

The reaction is preferably carried out in the liquid phase, it being possible for the total pressure to vary over wide limits, and the reaction temperature advantageously ranges from 100° to 240° C. and, preferably, from 160° to 190° C.

The carbon monoxide partial pressure typically ranges from 1 to 250 bar and, for very good results, it ranges from 2 to 100 bar.

The reaction mixture contains at least one solvent selected from among those indicated above, water, one or more sources of iridium, one or more iodinated promoters and, if need be, all or a part of the pentenic acid(s) involved and the products of the reaction.

Upon completion of the reaction or of the time allotted thereto, adipic acid is separated by any suitable means, for example by crystallization and filtration.

In order to further illustrate the present invention and the advantages thereof, the following specific examples are given, it being understood that same are intended only as illustrative and in nowise limitative.

EXAMPLE 1

The following materials were introduced into a glass flask purged beforehand with argon:
- (i) 30 mg (0.1 mmol) of iridium in the form of $Ir_4(CO)_{12}$;
- (ii) 0.045 g (0.2 mmol) of HI in the form of a solution in chlorobenzene (1 ml);
- (iii) 0.54 g (30 mmol) of water;
- (iv) 2 g (20 mmol) of penten-3-oic acid;
- (v) 9 cm³ of chlorobenzene.

The flask was placed into a 125 ml autoclave.

The autoclave was hermetically closed, placed into an oven equipped with means for agitation and connected to a supply of pressurized gas. 2 bar of CO were admitted while cold and the mixture was heated to 175° C. over 20 minutes. When this temperature was attained, the pressure was adjusted to 20 bar.

After a period of reaction of 30 minutes, the agitation and the heating were stopped; the autoclave was then cooled and degassed.

The reaction solution was analyzed by gas phase chromatography and by high performance liquid chromatography.

The amounts of products formed (molar yield in relation to penten-3-oic acid charged) were as follows:

valeric acid (Pa):  = 5% penten-2-oic acid (P2):  = 5%

γ-valerolactone (M4L): 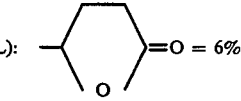 = 6% ethylsuccinic acid (A3):  = 2% methylglutaric acid (A2):  = 11% adipic acid (A1):  = 71%

The degree of linearity (L) was 84%. The degree of conversion of penten-3-oic acid (DC) was 93%.

EXAMPLE 2

The procedure of Example 1 was repeated, except that HI was introduced in the form of a solution (0.2 mmol) in acetic acid (1 ml).

All conditions being otherwise the same, substantially the same results were obtained except that the presence of penten-2-oic acid was no longer detected and that the molar yield of γ-valerolactone in relation to penten-3-oic acid charged (M4L) was 12.5%.

EXAMPLES 3 TO 6

Comparative Example (a)

The procedure of Example 1 was repeated using solvents of a different type and using a solution of HI (0.2 mmol) in acetic acid. The particular conditions as well as the results obtained are reported in Table I below, in which t represents the duration of the test at temperature.

TABLE I

| Example | Solvent (type) | t min | DC % | A1 % | L % | M4L % |
|---|---|---|---|---|---|---|
| 2 | Chlorobenzene | 30 | 93 | 71 | 84 | 12.5 |
| 3(*) | Methylene chloride | 35 | 100 | 70 | 84 | 10.0 |
| 4 | Toluene | 35 | 95 | 75 | 84 | 7.5 |
| 5 | Cyclohexane | 30 | 96 | 68 | 80 | 8 |
| 6 | Diphenyl ether | 40 | 100 | 63 | 78 | 12 |
| a | water/toluene (50/50 vol.) | 120 | 18 | ε | ND | 40 |

(*) In this Example, the total pressure at temperature was 30 bar.
ND: Not determined.

In Comparative Example (a), the formation of a predominant amount of pentanoic acid was recorded [PA (%)=40].

EXAMPLES 7 TO 8

Comparative Example (b)

According to the procedure described for Example 1, a series of tests was carried out in toluene and by modifying the amount of HI charged.

The particular conditions as well as the results obtained, all conditions being otherwise the same, are reported in Table II below, in which the conventions used are the same as for Example 1 and t again represents the duration of the test at temperature:

TABLE II

| Example | HI/Ir | t min | DC % | Al % | L % | M4L % |
|---|---|---|---|---|---|---|
| b | 0 | 90 | 0 | — | — | — |
| 1 | 2 | 30 | 93 | 71 | 84 | 6 |
| 7 | 5 | 35 | 99 | 44 | 78 | 33 |
| 8 | 9 | 85 | 78 | 21 | 81 | 65 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A process for the preparation of adipic acid, comprising reacting water and carbon monoxide with at least one pentenic acid, in the presence of a catalytically effective amount of an iridium-based catalyst and at least one iodinated promoter therefor at an elevated temperature, at a pressure greater than atmospheric and in at least one solvent medium which comprises a saturated aliphatic or cycloaliphatic hydrocarbon or halogenated derivative thereof, an aromatic hydrocarbon or halogenated derivative thereof, or an aliphatic, aromatic or mixed ether, and wherein the I/Ir atomic ratio is less than 10.

2. The process as defined by claim 1, said at least one pentenic acid comprising penten-3-oic acid, penten-2-oic acid, penten-4-oic acid, or mixture thereof.

3. The process as defined by claim 1, wherein the water/pentenic acid(s) molar ratio is less than or equal to 10.

4. The process as defined by claim 1, said solvent medium comprising benzene, toluene, chlorobenzene, hexane, cyclohexane, methylene chloride, 1,2-dichloroethane or diphenyl ether.

5. The process as defined by claim 1, said solvent medium constituting at least 10% by volume of the reaction mixture.

6. The process as defined by claim 5, said solvent medium constituting from 30% to 90% by volume of the reaction mixture.

7. The process as defined by claim 1, wherein the iridium concentration in the reaction mixture ranges from $10^{-3}$ to $10^{-1}$ mol/l.

8. The process as defined by claim 1, carried out at a temperature ranging from 100° to 240° C.

9. The process as defined by claim 1, wherein the carbon monoxide partial pressure ranges from 1 to 250 bar.

10. The process as defined by claim 1, said I/Ir atomic ratio being greater than or equal to 0.1.

11. The process as defined by claim 10, said I/Ir atomic ratio being from 1 to 5.

12. The process as defined by claim 1, said iodinated promoter comprising HI.

13. The process as defined by claim 8, carried out at a temperature ranging from 160° to 190° C.

14. The process as defined by claim 9, wherein the carbon monoxide partial pressure ranges from 2 to 100 bar.

* * * * *